(12) United States Patent
Song et al.

(10) Patent No.: US 10,076,312 B2
(45) Date of Patent: Sep. 18, 2018

(54) FILTER ASSEMBLY FOR MEDICAL IMAGE SIGNAL AND DYNAMIC DECIMATION METHOD USING SAME

(71) Applicant: SOGANG UNIVERSITY RESEARCH FOUNDATION, Seoul (KR)

(72) Inventors: Tai-Kyong Song, Seoul (KR); Hyungil Kang, Seoul (KR); Jeeun Kang, Seoul (KR)

(73) Assignees: Sogang Univeristy Research Foundation, Seoul (KR); HANSONO CO. LTD, Seoul (KR)

( * ) Notice: Subject to any disclaimer, the term of this patent is extended or adjusted under 35 U.S.C. 154(b) by 0 days.

(21) Appl. No.: 15/551,684

(22) PCT Filed: Dec. 3, 2015

(86) PCT No.: PCT/KR2015/013122
§ 371 (c)(1),
(2) Date: Aug. 17, 2017

(87) PCT Pub. No.: WO2016/133274
PCT Pub. Date: Aug. 25, 2016

(65) Prior Publication Data
US 2018/0035981 A1    Feb. 8, 2018

(30) Foreign Application Priority Data
Feb. 17, 2015    (KR) .................. 10-2015-0023981

(51) Int. Cl.
*G06F 17/17* (2006.01)
*A61B 8/08* (2006.01)
(Continued)

(52) U.S. Cl.
CPC .............. *A61B 8/5269* (2013.01); *A61B 8/08* (2013.01); *G01S 15/8977* (2013.01); *H03H 17/0664* (2013.01)

(58) Field of Classification Search
CPC ..... A61B 8/5269; A61B 8/08; G01S 15/8977; H03H 17/0664
(Continued)

(56) References Cited

U.S. PATENT DOCUMENTS

| 5,914,922 A * | 6/1999 | Supino ............... G11B 7/08541 |
|---|---|---|
| | | 369/44.28 |
| 2002/0031113 A1* | 3/2002 | Dodds ................. H04L 25/4908 |
| | | 370/352 |

(Continued)

FOREIGN PATENT DOCUMENTS

| JP | 2000-254122 | 9/2000 |
|---|---|---|
| JP | 2008-124593 | 5/2008 |

(Continued)

*Primary Examiner* — Tan V. Mai
(74) *Attorney, Agent, or Firm* — Duane Morris LLP; J. Rodman Steele, Jr.; Gregory M. Lefkowitz (57) ABSTRACT

The present invention relates to a filter assembly for a medical image signal and a dynamic decimation method using the same. The filter assembly includes a decimation filter that includes an integer number of multiplier accumulators (MACs), changes a cut-off frequency depending on a bandwidth of the medical image signal received through a dynamic impulse response update, and performs a decimation with respect to the received signal according to a decimation ratio, wherein the decimation filter determines a filter coefficient corresponding to an integer interval so as to up-sample the received medical image signal and supplies the filter coefficient to the MACs.

18 Claims, 5 Drawing Sheets

(51) Int. Cl.
*G01S 15/89* (2006.01)
*H03H 17/06* (2006.01)

(58) Field of Classification Search
USPC .......................................... 708/313
See application file for complete search history.

(56) References Cited

U.S. PATENT DOCUMENTS

2013/0109969 A1   5/2013   Kim et al.
2017/0077938 A1*  3/2017   Heubi ................... H03M 1/08

FOREIGN PATENT DOCUMENTS

| JP | 2012-182722 | 9/2012 |
|----|-------------|--------|
| KR | 1020000014092 | 3/2000 |
| KR | 1020040023927 | 3/2004 |
| KR | 1020080042729 | 5/2008 |
| KR | 1020110022440 | 3/2011 |
| KR | 101315891 | 10/2013 |
| KR | 1020140099567 | 8/2014 |

\* cited by examiner

FILTER ASSEMBLY FOR MEDICAL IMAGE SIGNAL AND DYNAMIC DECIMATION METHOD USING SAME

CROSS-REFERENCE TO RELATED APPLICATIONS

This application is a § 371 national stage entry of International Application No. PCT/KR2013/013122, filed on Dec. 3, 2015 which claims priority to South Korean Patent Application No. 10-2015-0023981, filed on Feb. 17, 2015, the entire contents of which are incorporated herein by reference.

TECHNICAL FIELD

The present invention relates to a technique of receiving and processing a medical image signal and, more particularly, a filter assembly for adaptively processing variation in bandwidth of an ultrasound image signal received from a probe according to depth of an image, and a dynamic decimation method using the same.

BACKGROUND ART

Medical imaging technology is a diagnosis technique of visually representing muscles, tendons, and many internal organs, to capture their size, structure, and pathologic lesions with real-time tomographic images, based on an ultrasound or photoacoustic means. Medical imaging is also used to visualize fetuses during a periodic checkup or in an emergency situation. Ultrasound has been used to image the interior of the human body for at least 50 years and has become one of the most widely used diagnostic tools in modern medicine. The ultrasound technique is low in cost and easy in mobility, relative to magnetic resonance imaging (MRI) or X-ray computed tomography (CT).

The principle of ultrasound imaging is as follows. First, an ultrasound image is made by bringing a measurement object into contact with a probe and receiving ultrasound reflected by generation of ultrasound waves. If ultrasound is generated, an ultrasound wave passes into a medium within a very short time and the ultrasound wave is reflected upon passing between two media having different acoustic impedances. In the ultrasound imaging technique, such a reflection wave is measured and a distance is calculated based on the time until reflection sound returns back, thereby achieving imaging.

In such ultrasound imaging, an echo signal returning from a target object attenuates according to depth and thus bandwidth of the signal varies. To improve a signal-to-noise ratio (SNR) caused by variation in bandwidth, a signal processing procedure is needed. An overview of ultrasound signal processing is given in the prior art document proposed below.

PRIOR ART DOCUMENT

Korean Patent Publication No. 10-2011-0022440, published on Mar. 7, 2011, Sogang University Research Foundation

DETAILED DESCRIPTION OF THE INVENTION

Technical Problems

The technical objects that can be achieved through the present invention are designed to solve inefficiency of a conventional filter structure for implementing dynamic decimation, in which filter length increases in proportion to a decimation ratio and thus there are wasted filters and multipliers that are not used according to dynamic variation of the decimation ratio and solve overhead of hardware cost and the amount of calculations necessary for multiplication at a high data rate because all multipliers are positioned after an expander.

Technical Solutions

According to an aspect of the present invention, provided herein is a filter assembly for a medical image signal, including an expander configured to receive the medical image signal and up-sample the medical image signal; and a decimation filter including an integer number of multiplier accumulators (MACs), configured to change a cutoff frequency according to bandwidth of the received medical image signal by dynamically updating an impulse response and perform decimation on the up-sampled signal according to a decimation ratio.

The decimation filter may calculate a partial sum, which is the sum of coefficients of a k-th (wherein k is a positive integer) location of a polyphase filter, through each MAC.

Each MAC may include a shift register configured to receive and store coefficients of a polyphase filter, a multiplier configured to multiply the coefficients stored in the shift register by the up-sampled signal, a summer configured to cumulatively sum the multiplied results, and a decimator configured to decimate the summed result.

A frequency band of the received signal may be determined by attenuation caused by depth of an object of the medical image signal and filter coefficients for calculating different cutoff frequencies according to the depth may be supplied to the MAC through the shift register to control a signal-to-noise ratio of the medical image.

Each MAC may include a fixed number of multipliers regardless of the decimation ratio to prevent waste of multipliers used according to variation in filter length.

In another aspect of the present invention, provided herein is a filter assembly for a medical image signal, including a decimation filter including an integer number of multiplier accumulators (MACs), configured to change a cutoff frequency according to bandwidth of the medical image signal by dynamically updating an impulse response and perform decimation on the received signal according to a decimation ratio, wherein the decimation filter determines a filter coefficient adjusted by an interval of an integer number to up-sample the medical image signal and supplies the filter coefficient to each MAC.

The medical image signal supplied to the decimation filter may not be previously up-sampled and operate at a low frequency relative to a previously up-sampled signal.

The decimation filter may determine, in consideration of an integer-fold expander for up-sampling, the filter coefficient so as to perform a partial sum calculation of the signal through the MAC except for a zero padding part out of an output of the expander.

The decimation filter may calculate a partial sum, which is the sum of coefficients of a k-th (where k is a positive integer) location of a polyphase filter, through the MAC.

The MAC may include a shift register configured to receive and store coefficients of a polyphase filter; a multiplier configured to multiply the coefficients stored in the shift register by the medical image signal; a summer configured to cumulatively sum the multiplied results; and a decimator configured to perform decimation on the summed result.

In another aspect of the present invention, provided herein is a method of decimating a medical image signal, including receiving the medical image signal; selecting a filter coefficient for changing a cutoff frequency according to bandwidth of the medical image signal in consideration of a decimation ratio; supplying the selected filter coefficient to a partial sum calculator including an integer number of multiplier accumulators (MACs); and performing, by the partial sum calculator, dynamic decimation on the received medical image signal, using the selected filter coefficient, wherein the filter coefficient is determined in consideration of an interval of an integer number to up-sample the received medical image signal.

The medical image signal supplied to the partial sum calculator may not be previously up-sampled and operate at a low frequency relative to a previously up-sampled signal.

The selecting the filter coefficient may include determining, in consideration of an integer-fold expander for up-sampling, the filter coefficient so as to calculate a partial sum through each MAC except for a zero padding part out of an output of the expander.

The partial sum calculator may calculate a partial sum, which is the sum of coefficients of a k-th (where k is a positive integer) location of a polyphase filter, through each MAC.

The performing dynamic decimation may includes multiplying, by the MAC, the medical image signal by coefficients of a polyphase filter stored in a shift register by use of a multiplier; cumulatively summing, by the MAC, the multiplied results by use of a summer; and decimating, by the MAC, the summed result by use of a decimator.

The MAC may include a fixed number of multipliers regardless of the decimation ratio to prevent waste of multipliers used according to variation in filter length.

Advantageous Effects

Embodiments of the present invention require relatively fewer hardware resources and less power consumption upon performing dynamic decimation by implementing a fixed number of multipliers by a polyphase filter structure and can achieve ultra-slimness of an ultrasound imaging system by adaptively applying a cutoff frequency of a filter in order to raise SNR.

DESCRIPTION OF REFERENCE NUMERALS

110: decimation filter
120: ultrasound imaging system
400: partial sum calculator including MAC
111, 210, 410, 610: expander
420: MAC
421: shift register
422: multiplier
423: register for summer
113, 424: decimator

BEST MODE FOR CARRYING OUT THE INVENTION

A filter assembly for a medical image signal according to an embodiment of the present invention includes an expander configured to receive the medical image signal and up-sample the medical image signal; and a decimation filter including an integer number of multiplier accumulators (MACs), configured to change a cutoff frequency according to bandwidth of the medical image signal by dynamically updating an impulse response and perform decimation on the up-sampled signal according to a decimation ratio.

MODE FOR INVENTION

Prior to a description of embodiments of the present invention, necessity and technical problems of a dynamic decimation filter will be briefly introduced and then a technical means adopted by the embodiments of the present invention in order to solve these problems will be proposed. Hereinbelow, among symbols represented in the description and drawings of the present invention, 'N' denotes the length of a filter, 'D' denotes a delay, 'L' denotes expansion increasing rate of an expander for up-sampling, and 'M' denotes a decimation ratio.

Figure 1:
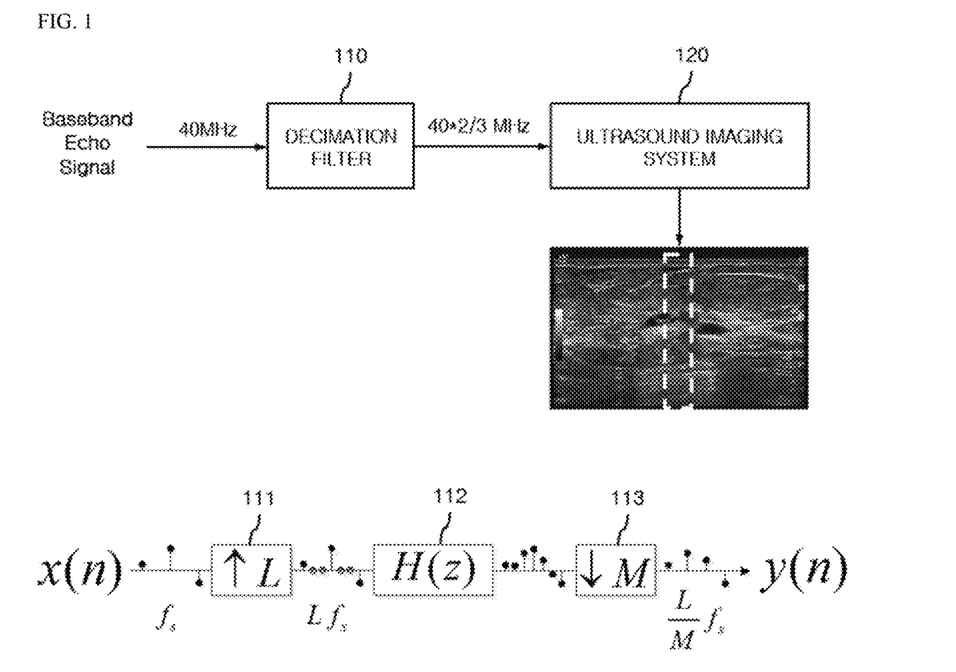
FIG. 1 is a diagram for explaining a decimation filter used in a medical imaging system through which embodiments of the present invention are implemented.

FIG. 1 is a diagram for explaining a decimation filter used in a medical imaging system through which embodiments of the present invention are implemented.

In medical ultrasound imaging, since an ultrasound signal is affected by frequency-dependent and depth-dependent attenuation while passing through soft tissues, center frequency and frequency bandwidth of an echo signal decrease with depth. In this case, a dynamic filter is used to maximize SNR as frequency bandwidth decreases and is mainly implemented by a decimation filter used generally to match the data rate of the echo signal to a screen. Accordingly, such a dynamic decimation filter should be capable of performing decimation on an arbitrary fractional decimation factor M/L and should be capable of dynamically updating an impulse response thereof.

Referring to (a) of FIG. 1, a decimation filter 110 adjusts the number of samples when the number of samples of a baseband signal is larger than the number of samples to be displayed on a screen through an ultrasound imaging system 120. In (a) of FIG. 1, it is assumed that 512 samples are needed per centimeter when 40 MHz-sampling is performed. Then, 2,048 to 10,240 samples are needed with respect to an image of 4 to 20 cm. Therefore, 1,024 samples are actually required for a display resolution of 640×480.

Referring to (b) of FIG. 1, in order to adjust the number of samples, an input signal x(n) is integer-fold up-sampled (111), signal-processed using a coefficient (112) of a decimation filter, and decimated (113) at a ratio of M, thereby generating an output signal y(n).

Meanwhile, as described above, the echo signal in medical ultrasound imaging is affected by depth-dependent attenuation and the bandwidth of the echo signal differs according to depth. Therefore, it is necessary to dynamically update a cutoff frequency with respect to each depth in order to maximize SNR. That is, the cutoff frequency varies with bandwidth using the dynamic filter. Typically, the length N of the filter is proportional to the cutoff frequency and the decimation ratio.

Figure 2:
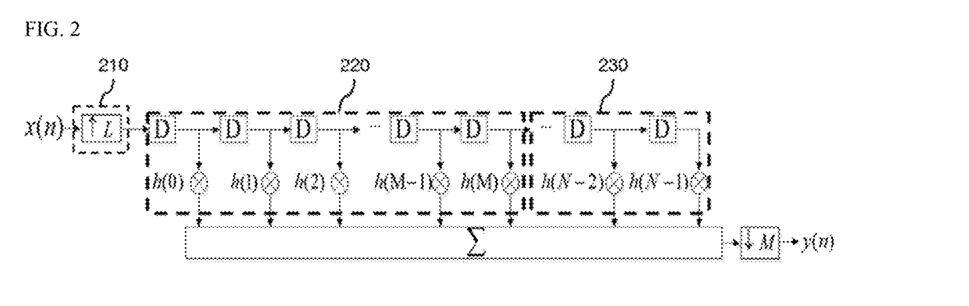
FIG. 2 is a diagram for explaining problems occurring upon dynamically performing decimation through a finite impulse response (FIR) filter.

FIG. 2 is a diagram for explaining problems occurring upon dynamically performing decimation through a finite impulse response (FIR) filter. The structure of an M/L-fold dynamic decimation filter is shown in FIG. 2.

In implementing a dynamic decimation filter structure using the FIR filter (when M>L), the length N of the filter increases in proportion to increase in the decimation ratio M. That is, a condition of N=KM may be assumed. Referring to FIG. 2, it may be appreciated that the filter length N is equal to the number of multipliers included in the filter and, due to characteristics of the dynamic decimation filter structure, a hardware filter should be implemented for a maximum decimation ratio. In this case, the number of multipliers used varies dynamically. For example, if a used part 220 includes (M+1) multipliers, multipliers (h(M+1) to h(N−1)=0) of the other part 230 are unused and wasted. That is, if a maximum value of M is large, the filter requires excessive multipliers and, if the value of M is small in a dynamic decimation processing procedure, many multipliers are wasted, thereby causing inefficiency.

In addition, since all multipliers are provided after an L-fold expander 210, the multipliers operate at a high operation frequency of L times and at a high data rate of L times. Therefore, the amount of calculations per unit time increases and thus overhead increases in terms of the amount of calculations of a block and hardware cost.

Figure 3:
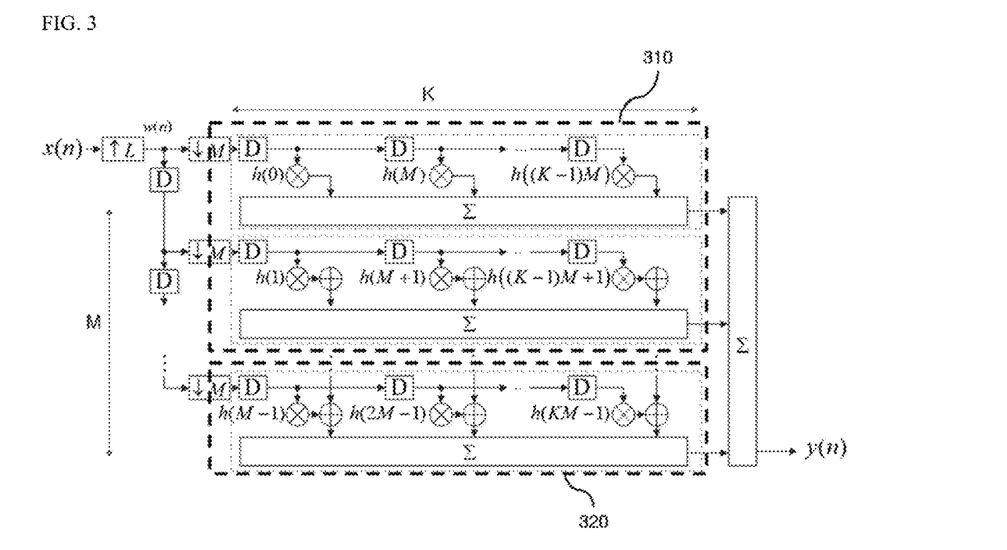
FIG. 3 is a diagram for explaining an example of implementing a decimation filter using a polyphase structure instead of the FIR filter of FIG. 2 and problems occurring in such an example.

FIG. 3 is a diagram for explaining an example of implementing a decimation filter using a polyphase structure instead of the FIR filter of FIG. 2 and problems occurring in such an example.

To efficiently improve the FIR filter introduced in FIG. 2, a dynamic decimation filter using a polyphase filter may be used. When the decimation filter shown in FIG. 3 is used, M-fold decimation is performed after performing L-fold expansion. Then, as compared with the dynamic decimation filter structure using the FIR filter, the filter of FIG. 3 has the same length as the filter of FIG. 2 but a data rate at which multipliers operate is lowered by M times.

However, even in this case, since multipliers proportional to the length of the filter are needed, there is waste of multipliers when the value of M is small. For example, if a part 310 which is used in a dynamic decimation process is small relative to a part 320 which is not used in the dynamic decimation process, inefficiency may occur in using hardware and resources.

Accordingly, embodiments of the present invention described hereinbelow propose a filter structure which has all functions of the above-described dynamic decimation filter and simultaneously can be efficiently implemented without waste of hardware and operation resources. That is, an efficient arbitrary factional decimation structure only using K multiplier accumulators is proposed to use restricted hardware complexity regardless of L and K. Hereinafter, the embodiments of the present invention will be described in detail with reference to the attached drawings.

An equation of a general FIR-based decimation filter is defined as follows. When an arbitrary fractional decimation factor is represented as M/L, a signal w(n) which is L-fold up-sampled with respect to an input x(n) is given as indicated in Equation 1.

$$w(n) = \begin{pmatrix} x(n/L), & n = pL\,(p\text{: integer}) \\ 0, & \text{otherwise } 0 \end{pmatrix} \qquad \text{[Equation 1]}$$

Herein, n is a sampling index. A procedure of filtering the FIR as shown in FIG. 2 with respect to such an input is indicated as Equation 2.

$$y(n) = \sum_{j=0}^{N-1} h(j) \cdot w(nM - j) \qquad \text{[Equation 2]}$$

Herein, h(j) denotes a coefficient of a given FIR filter and N denotes the length of the filter.

An equation for a dynamic decimation structure using the polyphase filter will now be defined. First, Equation 2 may be summarized as Equation 3 upon changing a dynamic decimation filter structure to a polyphase structure in which outputs of all polyphase filters are added as illustrated in FIG. 3.

$$y(n) = \sum_{k=0}^{K-1} H(k) \cdot W(n-k) = \qquad \text{[Equation 3]}$$

$$\sum_{k=0}^{K-1} \sum_{m=0}^{M-1} h(kM + m) \cdot w((n-k)M - m)$$

$$H(k) = [h(kM)\,h(kM+1)\,\ldots\,h(kM+M-1)]$$

$$W(n) = [w(nM)\,w(nM-1)\,\ldots\,w(nM-(M-1))]^T$$

Figure 4:
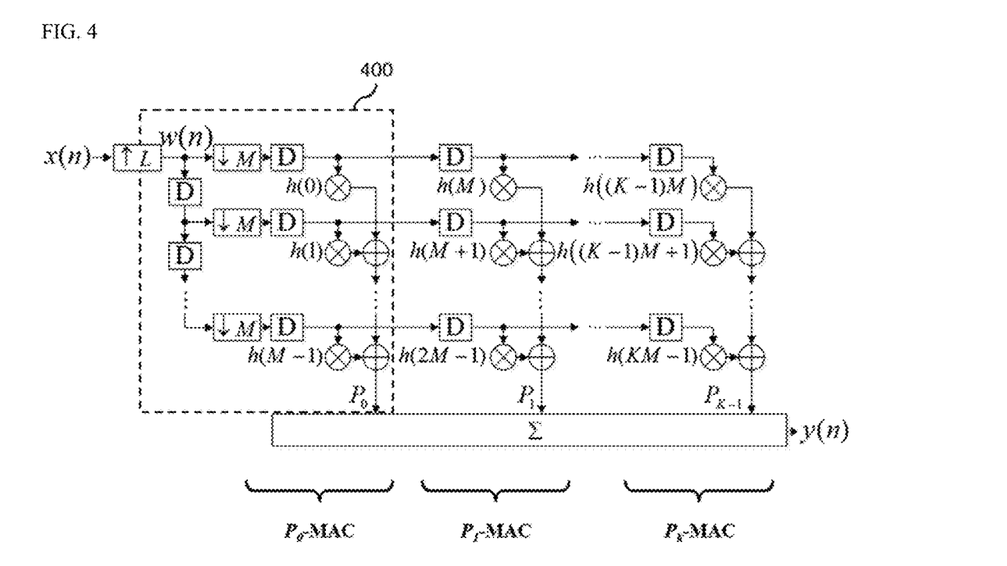
FIG. 4 is a diagram illustrating a decimation filter assembly implementing partial sums of phase filters using multiplier accumulators (MACs) according to an embodiment of the present invention.

FIG. 4 is a diagram illustrating a structure in which partial sums $P_0$ to $P_{k-1}$ are added based on k-th coefficients with respect to M polyphase filters of FIG. 3.

FIG. 4 is a diagram illustrating rearrangement of the polyphase filters of FIG. 3 through multiplier accumulators (MACs) according to an embodiment of the present invention. It may be appreciated that the polyphase filters are implemented through a plurality of $P_0$-MAC, $P_1$-MAC, . . . , $P_k$-MAC connected in parallel to each other.

Equation 3 indicates that each partial sum $P_k(n)$ in FIG. 4 is obtained by multiplying M consecutive pairs of input samples by filter coefficients at a data rate of $L \cdot f_x$ and cumulatively summing the multiplied results. Since each partial sum is calculated at a period of M samples through Equation 3, it will be appreciated that the partial sum can be implemented by a single MAC. Outputs of the MACs are summed to produce an output y(n) as indicated by Equation 4.

$$y(n) = \sum_{k=0}^{K-1} P_k(n-k) = \sum_{k=0}^{K-1}\sum_{m=0}^{M-1} w((n-k)M - m) \cdot h(kM + m)$$ [Equation 4]

$$P_k(n) = \sum_{m=0}^{M-1} w(nM - m) \cdot h(kM + m), k = 0, 1, \ldots, K-1$$

Each MAC that calculates each partial sum $P_k(n)$ is represented as $P_k$-MAC and all $P_k$-MAC units receive the same data set. This is implemented by eliminating delays between adjacent filter blocks illustrated in FIG. 3 and, instead, outputs of the MAC units are implemented as a delayed sum as indicated in Equation 4.

In summary, the filter assembly of FIG. 4 includes an expander for receiving a medical image signal and up-sampling the medical image signal and a decimation filter that includes an integer number of MACs, changes a cutoff frequency according to bandwidth of the medical image signal by dynamically updating an impulse response, and performs decimation on the up-sampled signal according to a decimation ratio. The decimation filter calculates a partial sum, which is the sum of coefficients of a k-th (wherein k is a positive integer) location of a polyphase filter, using each MAC.

More specifically, when the sum of coefficients of a k-th location of each polyphase filter is a partial sum $P_k$, this partial sum is implemented through a MAC expressed as $P_k$-MAC. Only a limited number of multipliers is used regardless of a decimation ratio M and the coefficients are supplied to the MAC through a shift register (not shown) to perform calculation.

Thus, calculation can be performed using only K (where K is a positive integer) multipliers using the MAC, as opposed to the multipliers used to match the filter length as in FIGS. 2 and 3. Therefore, if only the length of the coefficients supplied to the MAC is matched as the filter length varies, arbitrary fractional decimation can be performed only by a limited number of multipliers.

The amount of ultrasound reception signals varies according to depth of an image. For example, if the amount of reception data used to image a specific depth is 1,536, 1,024 samples are required to display the specific depth at a resolution of 640×480. Therefore, 3/2-fold decimation is needed. To efficiently perform decimation through a dynamic decimation filter having a filter length 32, M=3, and L=2, a sampling frequency of the reception signal is supplied to input of the filter and is supplied to 8 (K=8) P-MACs.

In addition, since a frequency band of a reception signal decreases according to depth, if a filter coefficient is updated in the shift register by calculating a different cutoff frequency according to depth, a filter having a maximum SNR can be constructed.

Figure 5:
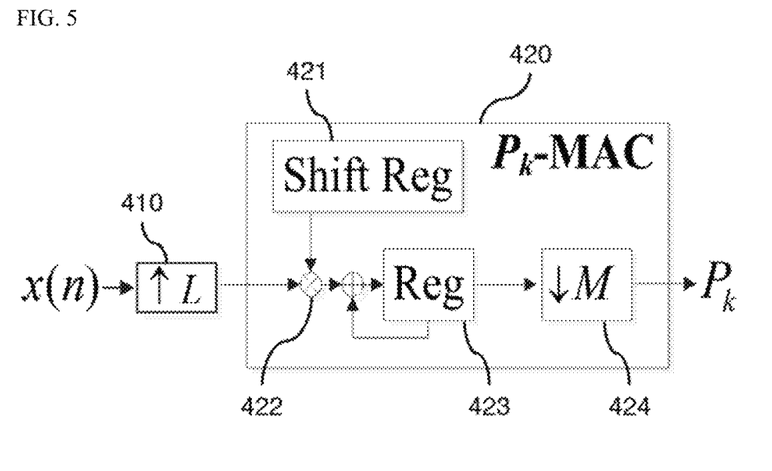
FIG. 5 is a block diagram illustrating in detail a partial sum calculator for calculating a k-th (wherein k is a positive integer) partial sum in the decimation filter assembly of FIG. 4 according to an embodiment of the present invention.

FIG. 5 is a block diagram illustrating in detail a partial sum calculator 400 for calculating a k-th (wherein k is a positive integer) partial sum in the decimation filter assembly of FIG. 4 according to an embodiment of the present invention. The partial sum calculator 400 includes an expander 410 and a $P_k$-MAC 420.

Each $P_k$-MAC cumulatively sums filter calculations with respect to an L-fold up-sampled input signal and outputs the summed result according to a decimation ratio. Thus, M filter coefficient calculations are performed by one multiplier. In this case, a filter coefficient of a shift register is adaptively applied according to the cutoff frequency.

More specifically, the $P_k$-MAC 420 includes a shift register 421 for receiving and storing coefficients of a polyphase filter, a multiplier 422 for multiplying the coefficients stored in the shift register 421 by the up-sampled signal, a summer and register 423 for cumulatively summing the multiplied results, and a decimator 424 for performing M-fold decimation on the summed result.

The frequency band of the reception signal is determined by attenuation caused by the depth of an object of the medical image signal. The $P_k$-MAC 420 calculates different cutoff frequencies according to the depth and supplies the filter coefficients to the shift register 421, thereby controlling an SNR of the medical image. Particularly, since the $P_k$-MAC 420 includes a fixed number of multipliers 422 regardless of the decimation ratio, the waste of multipliers used according to variation in the filter length is prevented.

An additional embodiment for improving performance of such a dynamic decimation filter structure in terms of an operation frequency will now be proposed.

Figure 6A:
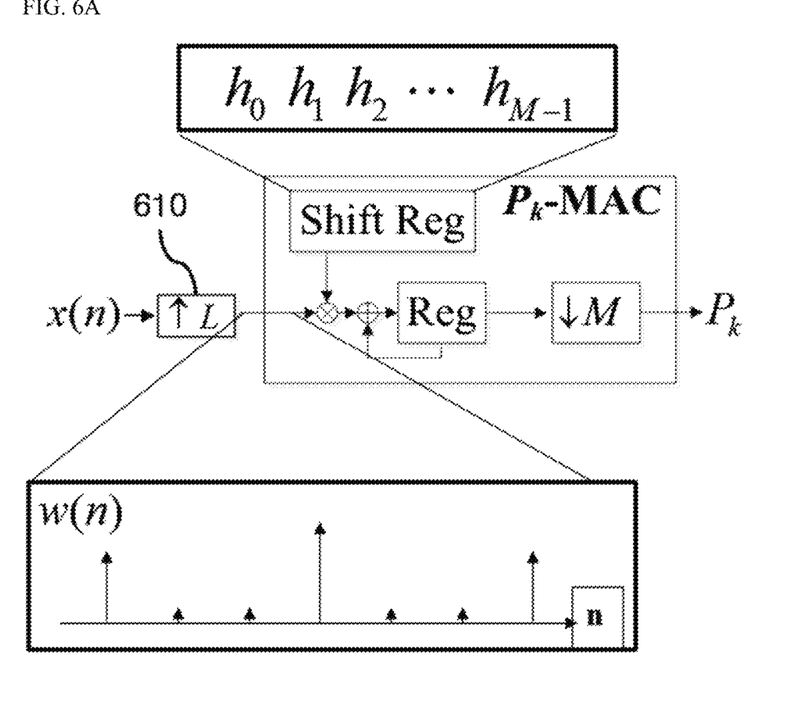
FIGS. 6A and 6B are diagrams for explaining a structure in which an expander is removed from the decimation filter assembly of FIG. 4.
Figure 6B:
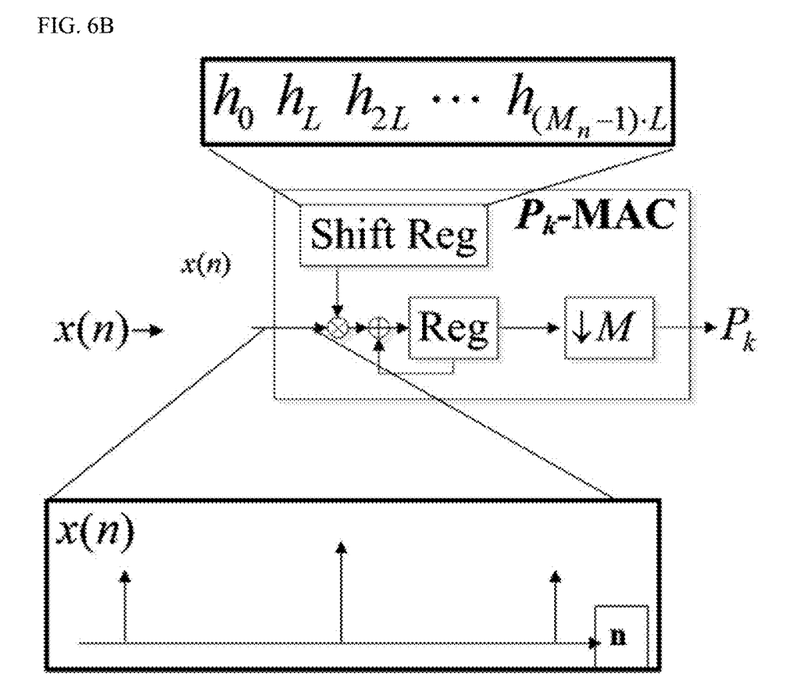

FIG. 6 is a diagram for explaining a structure in which an expander is removed from the decimation filter assembly of FIG. 4. (a) of FIG. 6 corresponds to the filter structure introduced in FIGS. 4 and 5.

Referring to (a) of FIG. 6, a medical image signal input to a Pk-MAC is a signal which is L-fold up-sampled by an expander 610. That is, it may be appreciated that the structure of (a) of FIG. 6 demands L-fold expansion with respect to input data.

To improve this, in (b) of FIG. 6, the expander 610 is removed and an L-fold up-sampling procedure is performed in the Pk-MAC so that a signal process procedure performed at a lower frequency may be derived. To this end, in (b) of FIG. 6, filter coefficients adjusted by an interval of L are supplied to a shift register and then is supplied to a multiplier.

To this end, a filter assembly for the medical image signal illustrated in (b) of FIG. 6 includes a decimation filter which includes an integer number of MACs, changes a cutoff frequency according to bandwidth of the medical image signal by dynamically updating an impulse response, and performs decimation on the received signal according to a decimation ratio. The decimation filter selects filter coefficients adjusted by an interval of an integer number in order to up-sample the medical image signal and supplies the selected filter coefficients to the MAC. Particularly, the medical image signal supplied to the decimation filter of (b) of FIG. 6 is not previously up-sampled and operates at a low frequency relative to a previously up-sampled signal.

More specifically, in consideration of an integer-fold expander for up-sampling, the decimation filter determines the filter coefficients such that the MAC may perform a partial sum calculation of a signal except for a zero padding part out of the output of the expander. That is, if the filter coefficients are adjusted to values other than 0 out of the output of the expander in consideration of the L-fold expander and are adaptively supplied to the MAC to match frequency bandwidth, the expander may be eliminated and a cutoff frequency matching input frequency bandwidth may be adaptively applied.

Obviously, the decimation filter of (b) of FIG. 6 also calculates a partial sum, which is the sum of coefficients of a k-th (where k is a positive integer) location of a polyphase filter, through the MAC. As described with reference to FIG. 5, the MAC includes a shift register for receiving and storing the coefficients of the polyphase filter, a multiplier for multiplying the coefficients stored in the shift register by the medical image signal, a summer for cumulatively summing the multiplied results, and a decimator for performing decimation on the summed result.

In this way, the decimation filter assembly of (b) of FIG. 6 requires fewer hardware resources and less power consumption by operating at a relatively low frequency and can prevent waste of multipliers according to variation of the filter length by using a fixed number of multipliers regardless of a decimation ratio.

Figure 7:
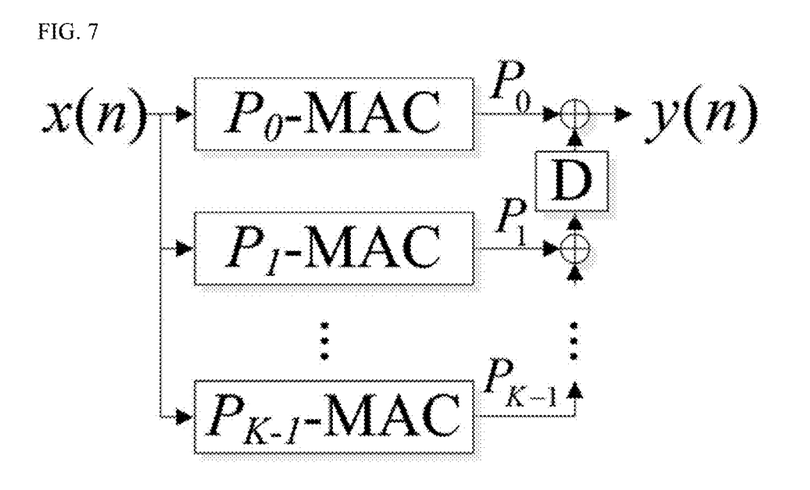
FIG. 7 is a block diagram for explaining a structure in which an expander is removed according to another embodiment of the present invention.

FIG. 7 is a block diagram illustrating a decimation filter assembly in which an expander is removed according to another embodiment of the present invention. To efficiently design filter length proportional to a decimation ratio M and the amount of calculations caused by an expander, a partial sum of a phase filter structure is implemented using MACs.

More specifically, an original input sequence x(n) is used as input of a Pk-MAC unit. Since it is assumed that decimation is performed, a non-zero value is necessarily present between M elements of w(n) of Equation 3 when M>L. In this case, w(nM−p)=x(q) (0≤p≤M−1) is satisfied (only when nM−p=qL and w(nM−m)=0 for m≠p). When l denotes the smallest value of p and n̂ denotes the largest value of q, l=nM mod L and n̂=⌊nM/L⌋. That is, x(n̂)=w(nM−l) indicates the first non-zero value of W(n). Therefore, if $M_n$ non-zero values are present in W(n), $M_n$ is the largest value of j satisfying l+(j−1)L≤M−1 and may be indicated as in Equation 5.

$$M_n = \left\lfloor \frac{M-1-l}{L} \right\rfloor + 1 \quad \text{[Equation 5]}$$

Since w(nM−l−jL)=x(n̂−j), an input data vector and a filter coefficient supplied to all MAC units are represented as in Equation 6 according to a Pk-MAC.

$$X(n)=[x(n̂)x(n̂-1) \ldots x(n̂-M_n+1)]^T,$$

$$H_k(l)=[h(kM+l)h(kM+l+L) \ldots h(kM+l(M_n-1)L)]^T \quad \text{[Equation 6]}$$

As illustrated in FIG. 7, MAC units output K partial sums $P_k(n)=X(n)\cdot H_k(l)$ (k=0, 1, . . . K−1). These partial sums are delayed through a delay chain as in $P_k(n-k)$ (k=0, 1, . . . K−1) and are summed to produce the output y(n) of Equation 4. Since X(n) has $M_n$ elements, the Pk-MAC outputs a partial sum after $M_n$ samples are input as illustrated by an $M_n$-fold decimator at an output stage of each MAC. If L and M are relatively prime, the sum of L consecutive values of $M_n$ having L repeated patterns is equal to M, i.e., $M_n+M_{n-1}+ \ldots +M_{n-L+1}=M$. Therefore, it can be appreciated that a decimation factor is M/L since the proposed structure provides L outputs per M input samples.

Figure 8:
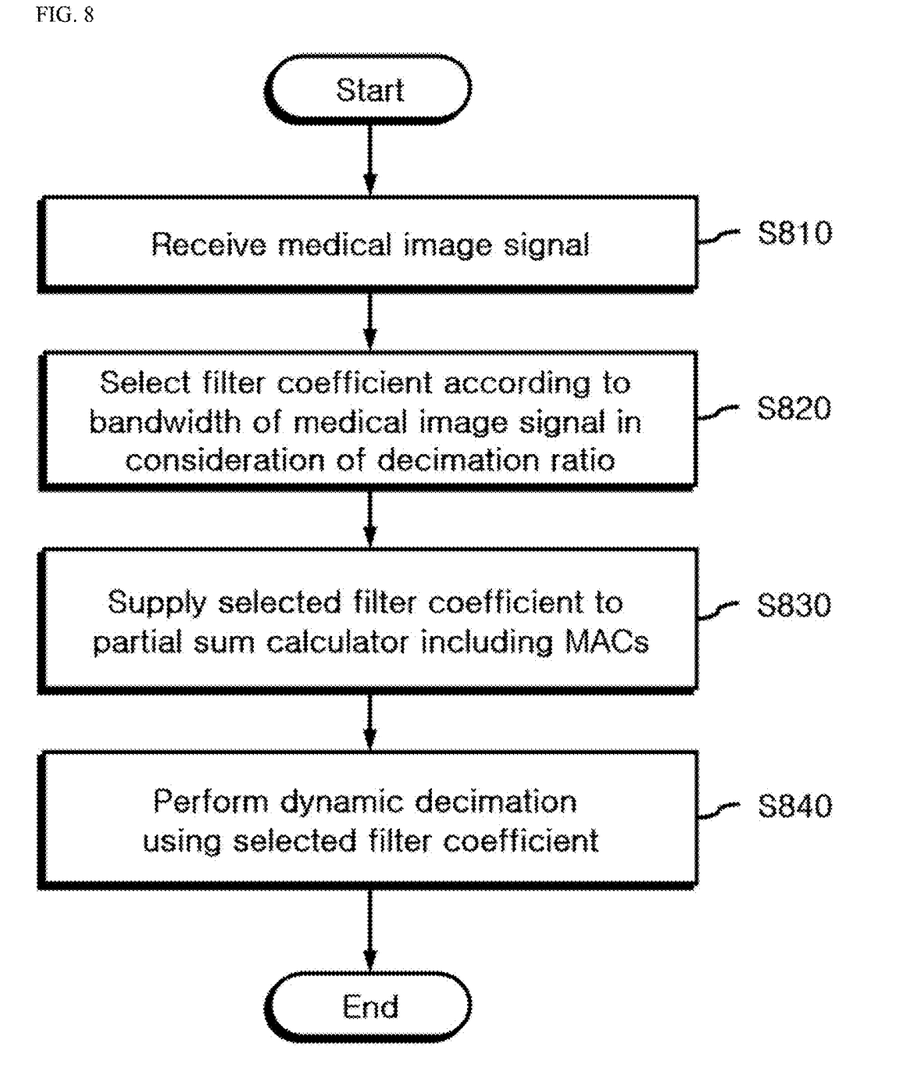
FIG. 8 is a flowchart illustrating a decimation method of a medical image signal using a dynamic decimation filter according to still another embodiment of the present invention.

FIG. 8 is a flowchart illustrating a decimation method of a medical image signal using a dynamic decimation filter according to still another embodiment of the present invention. Since the decimation method includes a procedure corresponding to each configuration of (b) of FIG. 6 described earlier, each process will be briefly described focusing on a time cause-and-effect relation of operations to avoid a repeated description.

In step S810, a medical image signal is received.

In step S820, a filter coefficient for changing a cutoff frequency is selected according to bandwidth of the medical image signal in consideration of a decimation ratio. In this case, in order to remove an expander, the filter coefficient is desirably determined in consideration of an interval of an integer number for up-sampling the medical image signal received in step S810. To this end, in step S820 for selecting the filter coefficient, it is desirable to select the filter coefficient such that a partial sum through a MAC is calculated except for a zero padding part out of the output of the expander in consideration of integer-fold expansion.

Accordingly, the medical image signal supplied to a partial sum calculator is not previously up-sampled and operates at a low frequency relative to a previously up-sampled signal.

In step S830, the determined filter coefficient is supplied to the partial sum calculator including an integer number of MACs. Herein, the partial sum calculator calculates a partial sum, which is the sum of coefficients of a k-th (where k is a positive integer) location of a polyphase filter, using the MAC. The MAC includes a fixed number of multipliers regardless of the decimation ratio, thereby preventing waste of multipliers according to variation in filter length.

In step S840, dynamic decimation is performed on the received medical image signal using the filter coefficients supplied by the partial sum calculator. More specifically, in step S840, the MAC multiplies the medical image signal by the coefficients of the polyphase filter stored in a shift register, by use of a multiplier, and cumulatively sums the multiplied results, and decimates the summed result using a decimator.

Meanwhile, the method for performing decimation on a medical image signal in processing a digital signal according to the foregoing exemplary embodiments may be implemented as code that can be written in a computer-readable recording medium and thus read by a computer system. The computer-readable recording medium may be any type of recording device in which data that can be read by the computer system is stored.

Examples of the computer-readable recording medium include a ROM, a RAM, a CD-ROM, a magnetic tape, a floppy disk, optical data storage, and a carrier wave (e.g., data transmission over the Internet). The computer-readable recording medium can be distributed over computer systems connected to a network so that computer-readable code is written thereto and executed therefrom in a decentralized manner. Functional programs, code, and code segments to realize the embodiments herein can be construed by one of ordinary skill in the art.

While the present invention has been particularly shown and described with reference to exemplary embodiments thereof, those skilled in the art will appreciate that the present invention may be embodied in other specific forms than those set forth herein without departing from the spirit and essential characteristics of the present invention. The above detailed description is therefore to be construed in all aspects as illustrative and not restrictive. The scope of the invention should be determined by reasonable interpretation of the appended claims and all changes coming within the equivalency range of the invention are within the scope of the invention.

INDUSTRIAL APPLICABILITY

According to the above-described embodiments of the present invention, a fixed number of multipliers is implemented as a polyphase filter structure using a MAC. Therefore, since relatively few hardware resources and less power consumption are needed upon performing dynamic decimation and a cutoff frequency of a filter is adaptively applied to raise SNR, ultra-slimness of an ultrasound imaging system can be achieved.

The invention claimed is:

1. A filter assembly for a medical image signal, comprising:
   an expander configured to receive the medical image signal and up-sample the medical image signal; and
   a decimation filter including an integer number of multiplier accumulators (MACs), configured to change a cutoff frequency according to bandwidth of the received medical image signal by dynamically updating an impulse response and perform decimation on the up-sampled signal according to a decimation ratio.

2. The filter assembly according to claim 1, wherein the decimation filter calculates a partial sum, which is the sum of coefficients of a k-th (wherein k is a positive integer) location of a polyphase filter, through each MAC.

3. The filter assembly according to claim 1, wherein each MAC includes:
   a shift register configured to receive and store coefficients of a polyphase filter;
   a multiplier configured to multiply the coefficients stored in the shift register by the up-sampled signal;
   a summer configured to cumulatively sum the multiplied results; and
   a decimator configured to decimate the summed result.

4. The filter assembly according to claim 3, wherein a frequency band of the received signal is determined by attenuation caused by depth of an object of the medical image signal and filter coefficients for calculating different cutoff frequencies according to the depth are supplied to the MAC through the shift register to control a signal-to-noise ratio of the medical image.

5. The filter assembly according to claim 1, wherein each MAC includes a fixed number of multipliers regardless of the decimation ratio to prevent waste of multipliers used according to variation in filter length.

6. A filter assembly for a medical image signal, comprising:
   a decimation filter including an integer number of multiplier accumulators (MACs), configured to change a cutoff frequency according to bandwidth of the medical image signal by dynamically updating an impulse response and perform decimation on the received signal according to a decimation ratio,
   wherein the decimation filter determines a filter coefficient adjusted by an interval of an integer number to up-sample the medical image signal and supplies the filter coefficient to each MAC.

7. The filter assembly according to claim 6, wherein the medical image signal supplied to the decimation filter is not previously up-sampled and operates at a low frequency relative to a previously up-sampled signal.

8. The filter assembly according to claim 6, wherein the decimation filter determines, in consideration of an integer-fold expander for up-sampling, the filter coefficient so as to perform a partial sum calculation of the signal through the MAC except for a zero padding part out of an output of the expander.

9. The filter assembly according to claim 6, wherein the decimation filter calculates a partial sum, which is the sum of coefficients of a k-th (where k is a positive integer) location of a polyphase filter, through the MAC.

10. The filter assembly according to claim 6, wherein the MAC includes:
    a shift register configured to receive and store coefficients of a polyphase filter;
    a multiplier configured to multiply the coefficients stored in the shift register by the medical image signal;
    a summer configured to cumulatively sum the multiplied results; and
    a decimator configured to perform decimation on the summed result.

11. The filter assembly according to claim 10, wherein a frequency band of the received signal is determined by attenuation caused by depth of an object of the medical image signal and filter coefficients for calculating different cutoff frequencies according to the depth are supplied to the MAC through the shift register to control a signal-to-noise ratio of the medical image.

12. The filter assembly according to claim 6, wherein the MAC includes a fixed number of multipliers regardless of the decimation ratio to prevent waste of multipliers used according to variation in filter length.

13. A method of decimating a medical image signal, comprising:
    receiving the medical image signal;
    selecting a filter coefficient for changing a cutoff frequency according to bandwidth of the medical image signal in consideration of a decimation ratio;
    supplying the selected filter coefficient to a partial sum calculator including an integer number of multiplier accumulators (MACs); and
    performing, by the partial sum calculator, dynamic decimation on the received medical image signal, using the selected filter coefficient,
    wherein the filter coefficient is determined in consideration of an interval of an integer number to up-sample the received medical image signal.

14. The method according to claim 13, wherein the medical image signal supplied to the partial sum calculator is not previously up-sampled and operates at a low frequency relative to a previously up-sampled signal.

15. The method according to claim 13, wherein the selecting the filter coefficient includes determining, in consideration of an integer-fold expander for up-sampling, the filter coefficient so as to calculate a partial sum through each MAC except for a zero padding part out of an output of the expander.

16. The method according to claim 13, wherein the partial sum calculator calculates a partial sum, which is the sum of coefficients of a k-th (where k is a positive integer) location of a polyphase filter, through each MAC.

17. The method according to claim 13, wherein the performing dynamic decimation includes:
    multiplying, by the MAC, the medical image signal by coefficients of a polyphase filter stored in a shift register by use of a multiplier;
    cumulatively summing, by the MAC, the multiplied results by use of a summer; and
    decimating, by the MAC, the summed result by use of a decimator.

18. The method according to claim 13, wherein the MAC includes a fixed number of multipliers regardless of the decimation ratio to prevent waste of multipliers used according to variation in filter length.

* * * * *